(12) United States Patent
Ancel et al.

(10) Patent No.: US 6,410,737 B1
(45) Date of Patent: Jun. 25, 2002

(54) PROCESSES FOR PREPARING PESTICIDAL INTERMEDIATES

(75) Inventors: Jean-Erick Ancel, Saint-Genis-Laval; Gilles Perrin-Janet, Chaponnay; Manuel Vangelisti, Lyons; Pierre Versproumy, Villeurbanne, all of (FR)

(73) Assignee: Aventis CropScience, S.A., Lyons (FR)

( * ) Notice: Subject to any disclaimer, the term of this patent is extended or adjusted under 35 U.S.C. 154(b) by 0 days.

(21) Appl. No.: 09/937,816

(22) PCT Filed: Mar. 30, 2000

(86) PCT No.: PCT/EP00/03103

§ 371 (c)(1), (2), (4) Date: Jan. 4, 2002

(87) PCT Pub. No.: WO00/59862

PCT Pub. Date: Oct. 12, 2000

(30) Foreign Application Priority Data

Mar. 31, 1999 (GB) .............................................. 9907458

(51) Int. Cl.⁷ ..................... C07C 211/28; C07D 213/02
(52) U.S. Cl. ........................ 546/311; 564/305; 564/442
(58) Field of Search .......................... 546/311; 564/305, 564/442

(56) References Cited

U.S. PATENT DOCUMENTS

| | | | |
|---|---|---|---|
| 4,096,185 A | 6/1978 | Seiwell | 260/581 |
| 4,535,154 A | 8/1985 | Keefer et al. | 544/106 |
| 5,082,945 A | 1/1992 | Wakselman et al. | 518/110 |
| 5,232,940 A | 8/1993 | Hatton et al. | 514/407 |
| 5,437,853 A | 8/1995 | Johnson et al. | 423/352 |
| 5,814,652 A | 9/1998 | Wu | 514/404 |

FOREIGN PATENT DOCUMENTS

| | | |
|---|---|---|
| EP | 0234119 A1 | 9/1987 |
| EP | 0295117 A1 | 12/1988 |
| EP | 0303906 A1 | 2/1989 |
| EP | 0374061 A1 | 6/1990 |

OTHER PUBLICATIONS

English abstract of Lunn et al, "Reductive destruction of hydrazines as an approach to hazard control," *Environ. Sci. Technol.*, 17(4), pp. 240–243 (1983), STN Database accession No. 98:113107, XP002143919.

Abstract of Arbusow et al, "Über die katalytische Spaltung des Phenylhydrazins durch monohaloide Kupfersalze", *Chemische Berichte.*, vol. 43, pp 2295–2296 (1910), XP002143918.

*Primary Examiner*—Zinna Northington Davis
(74) *Attorney, Agent, or Firm*—Burns, Doane, Swecker & Mathis, L.L.P.

(57) ABSTRACT

Compounds of formula (I) are prepared by hydrogenolysis of a compound of formula (II):

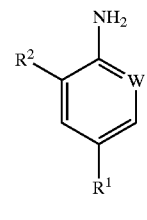

(I)

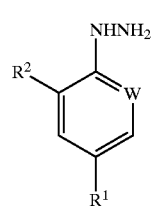

(II)

where $R^1$ is haloalkyl, haloalkoxy or $-SF_5$; W is N or $CR^3$; and $R^2$ and $R^3$ are H or Cl. The compounds of formula (I) can be used as intermediates in the preparation of pesticidally active arylpyrazole compounds.

16 Claims, No Drawings

PROCESSES FOR PREPARING PESTICIDAL INTERMEDIATES

This application is a 371 of PCT/EP00/03103 filed Mar. 30, 2000.

BACKGROUND OF THE INVENTION

This invention relates to novel processes for preparing intermediates (particularly certain arylamine compounds and arylhydrazine derivatives) useful in the preparation of pesticides.

DESCRIPTION OF THE RELATED ART

European Patent Publication Nos. 0295117 and 0234119 describe the preparation of pesticidally active phenylpyrazole compounds and of 5-amino-1-aryl-3-cyanopyrazole intermediate compounds used in their synthesis. Various methods for preparing these compounds are known. The present invention seeks to provide improved or more economical methods for the preparation of pesticides and the intermediate compounds useful in preparing them. 4-Trifluoromethylaniline, 2-chloro-4-trifluoromethylaniline and 2,6-dichloro-4-trifluoromethylaniline are valuable compounds used for the synthesis of pesticidally active phenylpyrazole compounds. A number of methods are known for preparing these compounds. However these procedures are expensive and the compounds are difficult to prepare requiring multi-step synthetic procedures. For example US patent publication number 4096185 describes the preparation of 4-trifluoromethylaniline by the reaction of 4-chlorobenzotrifluoride with ammonia at 200° C. in the presence of potassium fluoride and cuprous chloride in a Hastelloy vessel. There remains a need to develop new methods for obtaining these compounds.

SUMMARY OF THE INVENTION

The present applicants have surprisingly discovered novel processes for the preparation of certain substituted arylamines and arylhydrazines, thus providing a new method for preparing important 5-amino-1-aryl-3-cyanopyrazole compounds which are valuable intermediates for the preparation of pesticides.

The present invention accordingly provides a process (A) for the preparation of a

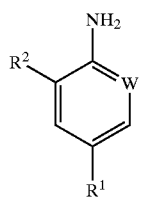

compound of formula (I):
wherein $R^1$ is haloalkyl (preferably trifluoromethyl), haloalkoxy (preferably trifluoromethoxy) or $-SF_5$;

W is N or $CR^3$; and $R^2$ and $R^3$ are each independently hydrogen or chlorine;
or an acid addition salt thereof; which process comprises the hydrogenolysis of a compound of formula (II):

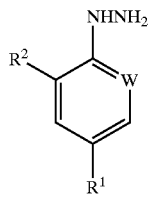

or an acid addition salt thereof, with a metal or metal compound (for example a metal salt) under reducing conditions.

DETAILED DESCRIPTION OF THE PREFERRED EMBODIMENTS

Certain compounds of formula (I) and (II) are novel and as such form a feature of the present invention.

Unless otherwise specified in the present invention 'haloalkyl' and 'aloalkoxy' are straight- or branched- chain alkyl or alkoxy respectively having from one to three carbon atoms substituted by one or more halogen atoms selected from fluorine, chlorine and bromine.

The acid addition salts referred to in the invention are preferably the salts formed from strong acids such as mineral acids, for example sulphuric acid or hydrochloric acid.

The hydrogenolysis may be performed using a metal or metal salt selected from Raney nickel (a nickel-aluminium alloy) optionally in the presence of iron, manganese, cobalt, copper, zinc or chromium; stannous chloride; zinc in the presence of acetic acid; and a molybdenum (III) salt. The reaction may also be carried out using Raney nickel, platinum or palladium (which may be supported on charcoal or other inert material) in the presence of hydrogen gas. When the reaction is performed with hydrogen gas a pressure of 2 to 20 bars (preferably 5 to 10 bars) is generally used. The hydrogenolysis is preferably performed using Raney nickel.

The reaction is generally conducted in a solvent which may be selected from alcohols such as methanol or ethanol; ethers; and aromatic hydrocarbons (methanol and ethanol are preferred solvents).

The reaction temperature is generally from 20° C. to 1 50° C., preferably from 20° C. to 90° C., more preferably from 50° C. to 80° C. The amount of catalyst employed is generally from 0.01 to 3 molar equivalents (preferably from 0.05 to 2 molar equivalents), although when the reaction is carried out under an atmosphere of hydrogen, a smaller amount generally gives satisfactory results.

In formulae (I) and (II) and in-the formulae depicted hereinafter $R^1$ preferably represents trifluoromethyl, trifluoromethoxy or $-SF_5$, more preferably trifluoromethyl.

Particularly preferred compounds of formula (I) are 2,6-dichloro-4-trifluoromethylaniline; 2-chloro-4-trifluoromethylaniline; and 4-trifluoromethylaniline. Process (A) seeks to enable arylamine compounds of formula (I) to be obtained in high yield from readily available starting materials. Furthermore the reaction can be very simple and economical to perform, and product isolation can be straightforward. Another advantage of this method is that the compounds of formula (I) may be prepared at moderate temperatures and pressures, whereas prior art methods require high temperatures.

If necessary the compounds of formula (I) may be purified by crystallisation, for example from petroleum ether, to remove unwanted isomer products which may be present in small amounts. Alternatively crystallisation at a later stage in the synthetic scheme may be effective.

The compounds of formula (II) can be obtained by a process (B) wherein a compound of formula (III):

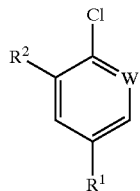

is reacted with hydrazine or an acid addition salt or source thereof.

Compounds of formula (III) are known or may be prepared by known methods.

According to a further feature of the invention process (A) can be combined with a process (B) to prepare a compound of formula (I) from a compound of formula (III).

Preferably hydrazine hydrate is used in the process (B).

When an acid addition salt of hydrazine is employed a base such as a trialkylamine (for example triethylamine) is optionally present.

Particularly preferred compounds of formula (II) are 2,6-dichloro-4-trifluoromethylphenylhydrazine; 2-chloro-4-trifluoromethylphenylhydrazine; and 4-trifluoromethylphenylhydrazine.

The process (B) may be conducted in a solvent chosen from cyclic or aliphatic ethers such as tetrahydrofuran, 1,4-dioxan or 1,2-dimethoxyethane; N-methylpyrrolidone; dimethyl sulphoxide; N,N-dimethylformamide; sulpholane; N,N,N',N'-tetramethylurea; aromatic hydrocarbons which may be substituted with one or more alkyl groups or chlorine atoms, such as chlorobenzene or xylene;

alcohols such as isopropanol; and pyridine. Preferred solvents include pyridine, tetrahydrofuran, N,N,N',N'-tetramethylurea and 1,4-dioxan (pyridine and tetrahydrofuran are especially preferred). The amount of solvent used is generally from 1 to 10 ml (preferably from 4 to 8 ml). per gramme of compound of formula (III).

The process (B) is generally performed in an autoclave or other sealed vessel. A pressure of from 1–8 bars (preferably 2–6 bars) is generally used.

The reaction temperature for process (B) is generally from 50° C. to 250° C., preferably from 120° C. to 180° C. A most preferred reaction temperature is from 120° C. to 150° C., when vessel corrosion and thermal decomposition of the product is minimal.

The reaction is generally conducted using from 1 to 20 molar equivalents (preferably 4 to 8 molar equivalents) of the hydrazine source.

A catalyst may optionally be used in the process (B), and when present is generally chosen from alkali and alkaline earth metal fluorides such as potassium fluoride. The amount of catalyst employed is generally from 0.05 to 2 molar equivalents (preferably from 0.5 to 1 molar equivalents). The reaction may also be effected in the presence of copper or a copper salt, preferably copper (I) chloride.

According to a further feature of the invention, process (A), or the combined processes (A) and (B), to give a compound of formula (I), which is purified by precipitation of the salt formed by treatment with a strong acid in the presence of an organic solvent.

The combined process (A) and (B) of the invention is particularly valuable when used for the preparation and reaction of the important intermediate 2-chloro-4-trifluoromethylphenylhydrazine, because the process step (B) proceeds in high yield and provides together with the other processes of the present invention an efficient method for obtaining important pesticidal phenylpyrazole compounds. However the preparation of 2-chloro-4-trifluoromethylphenylhydrazine often leads to a small amount of the unwanted 2-chloro-5-trifluoromethylphenylhydrazine as contaminant in addition to the desired isomer. It has been found that this mixture may be used directly in the following process (A) with subsequent purification. The purification of 2-chloro-4-trifluoromethylaniline may be achieved by precipitation of the salt formed with a strong acid, preferably the hydrochloride salt, in the presence of an organic solvent. The hydrochloride salts may be obtained using hydrogen chloride gas or aqueous hydrochloric acid. The solvent is generally an alcohol, preferably ethanol, or a halogenated aromatic compound, preferably chlorobenzene, or a mixture thereof. This procedure results in very efficient removal of the unwanted 2-chloro-5-trifluoromethylaniline isomer with precipitation of the desired isomer as 2-chloro-4-trifluoromethylaniline hydrochloride salt, in high yield and high purity.

Thus according to a preferred feature of the invention, process (A), or the combined processes (A) and (B), in which $R^1$ is trifluoromethyl, W is $CR^3$, $R^2$ is chlorine and $R^3$ is hydrogen, to give a compound of formula (I), which is purified by precipitation of the salt formed by treatment with a strong acid in the presence of an organic solvent.

Moreover when process (B) is used for the preparation of 4-trifluoromethylphenylhydrazine, in which the reactant (4-chlorobenzotrifluoride) is particularly unreactive, the reaction proceeds with excellent regioselectivity. In addition the use of catalysts has been found to increase the rate of the reaction. In this instance no product isomers can exist, and so the process when combined with subsequent stages provides a further useful method for obtaining important pesticidal phenylpyrazole compounds.

As indicated a particular advantage of the invention is that it allows the efficient preparation of compounds of formula (I) wherein one or both of $R^2$ and $R^3$ represent a hydrogen atom.

According to a preferred feature of the invention the process (A), or the combined processes (A) and (B), is followed by a process (C) which process comprises the reaction of the compound of formula (I) wherein W is N or $CR^3$ and one or both of $R^2$ and $R^3$ represent a hydrogen atom, with a chlorinating agent to replace the or each hydrogen atom represented by $R^2$ and $R^3$ and give the corresponding compound of formula (I) wherein $R^2$ and $R^3$ each represent a chlorine atom. The chlorination may be performed using chlorine gas or sulphuryl chloride in an inert solvent such as a halogenated hydrocarbon for example dichloromethane, according to known procedures.

According to a further feature of the invention the process (A), or the combined processes (A) and (B), (A) and (C), or (A), (B) and (C) can be combined with further process steps (D) in which the compound of formula (I) is diazotised to give a compound of formula (IV):

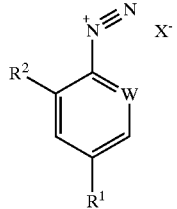

(IV)

wherein X is an anion generally hydrogen sulphate or chloride, which is reacted with a compound of formula (V):

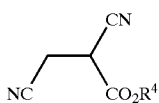

(V)

wherein $R^4$ is $C_{1-6}$ alkyl, and optionally reacted with a base to prepare a compound of formula (VI):

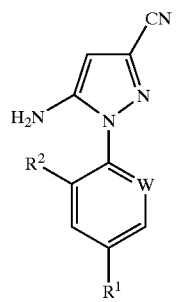

(VI)

wherein $R^1$, $R^2$ and W are as hereinbefore defined.

The above processes for the preparation of compounds of formula (VI) according to the invention, in combination with the above reaction steps for conversion of compounds of formula (III) into compounds of formula (II) and (I) provide an advantageous new synthetic route.

According to a further feature of the invention the combined processes (A) and (D); (A), (C) and (D); (A), (B) and (D); or (A), (B), (C) and (D), can be combined with further process steps (E) to prepare a compound of formula (VII):

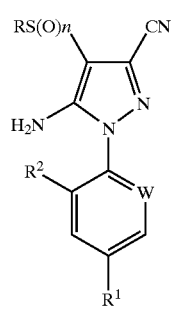

(VII)

wherein R is alkyl or haloalkyl and n is 0, 1 or 2. Especially preferred compounds of formula (VII) are 5-amino-1-(2,6-dichloro-4-trifluoromethylphenyl)-3-cyano-4-trifluoromethylsulphinylpyrazole (fipronil) and 5-amino-1-(2,6-dichloro-4-trifluoromethylphenyl)-3-cyano-4-ethylsulphinylpyrazole (ethiprole). The process steps (E) are known, for example as described in European Patent Publication Nos. 0295117 and 0374061, and U.S. Patent Publication No. 5814652.

The compounds of formula (I) obtained by the process (A) of the invention are particularly useful in the preparation of pesticidally active 5-amino-1-aryl-3-cyanopyrazole derivatives of formula (VII) obtained from intermediate compounds of formula (VI), for example, according to the following reaction scheme:

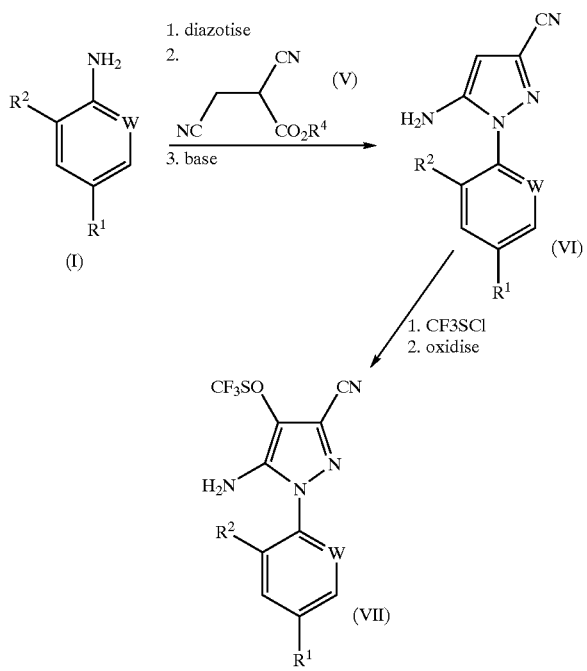

wherein $R^1$, $R^2$, $R^3$ and $R^4$ are as hereinbefore defined.

The following non-limiting examples illustrate the invention. Each product was shown to be identical to a known reference sample of the compound.

EXAMPLE 1

Preparation of 4-Trifluoromethylaniline

Raney nickel (2 g) was added to a solution of 4-trifluoromethylphenylhydrazine (1 g) in methanol (5 ml) and heated at reflux for 1 hour. The cooled mixture was filtered and evaporated to give the title compound in 100% yield.

EXAMPLE 2

Preparation of 2-Chloro-4-Trifluoromethylaniline

The procedure of Example 1 was repeated but using 2-chloro-4-trifluoromethylphenylhydrazine, to give the title compound in 100% yield.

EXAMPLE 3

Preparation 4-Trifluoromethylaniline

The procedure of Example 1 was repeated but using a catalytic amount of Raney nickel in methanol (8–10 ml per mmole of 4-trifluoromethylphenylhydrazine) under an atmosphere of hydrogen (5 bars) with stirring at 20° C. for 2 hours. The mixture was filtered and evaporated to give the pure title compound in 75% yield (unoptimised).

By proceeding in a similar manner there were also prepared with similar results:

2-chloro-4-trifluoromethylaniline; and 2,6-dichloro4-trifluoromethylaniline.

EXAMPLE 4

Preparation of 4-Trifluoromethylphenylhydrazine

A mixture of 4-chlorobenzotrifluoride (1.08 g), hydrazine hydrate (1.8 g, 6 molar equivalents) and pyridine (5 ml) was heated in an autoclave (purged with argon) for 6 hours at 180° C. The mixture was cooled, the excess hydrazine decanted and the organic phase evaporated in vacuo. The residue was crystallised from petroleum ether to give the title compound in 20% yield. It was shown that 20% of the starting material had been consumed, thus indicating that the reaction had occurred with high selectivity.

EXAMPLE 5

Preparation of 4-Trifluoromethylphenylhydrazine Using Potassium Fluoride as Catalyst The procedure of Example 4 was repeated but with the addition of potassium fluoride (0.8 molar equivalent) to give the title compound in 30% yield. It was shown that 30% of the starting material had been consumed, thus indicating that the reaction had occurred with high selectivity.

The above reaction was repeated but using N,N,N',N'-tetramethylurea as solvent to give the title compound in 40% yield. It was shown that 40% of the starting material had been consumed, thus indicating that the reaction had occurred with high selectivity.

EXAMPLE 6

Preparation of 4-Trifluoromethylphenylhydrazine Using Potassium Fluoride and Copper (I) Chloride as Catalyst The procedure of Example 4 was repeated but with the addition of potassium fluoride (0.1 molar equivalent) and copper (I) chloride (0.1 molar equivalent) to give the title compound in 14% yield. It was shown that 14% of the starting material had been consumed, thus indicating that the reaction had occurred with high selectivity.

EXAMPLE 7

Preparation of 2-Chloro-4-Trifluoromethylphenylhydrazine

The procedure of Example 4 was repeated but using 3,4-dichlorobenzotrifluoride. After work up there was isolated a 95% yield of the title compound. It was shown that 100% of the starting material had been consumed, thus indicating that the reaction had occurred with both high selectivity and high yield.

The above reaction was repeated but using various other solvents. The following yields of title compound were obtained:

| SOLVENT | % YIELD |
|---|---|
| tetrahydrofuran | 90 |
| 1,4-dioxan | 93 |
| N,N,N',N'-tetramethylurea | 72 |

EXAMPLE 8

Two Step Preparation and Purification of 2-Chloro-4-Trifluoromethylaniline Starting from 3,4-Dichlorobenzotrifluoride (a) A mixture of 3,4-dichlorobenzotrifluoride (48 g), hydrazine hydrate (65 g) and pyridine (240 g) was stirred and heated at 150° C. for 6 hours in an autoclave at a pressure of 4 bar. The cooled mixture was quenched with sodium hydroxide solution and the organic layer evaporated in vacuo. The residue was dissolved in diethyl ether, washed (water) and the ether evaporated to give 2-chloro-4-trifluoromethylphenylhydrazine and 2-chloro-5-trifluoromethylphenylhydrazine as a 95/5 mixture (36 g), (b) Raney Nickel (0.7 g) was added to a solution of the above isomer mixture (35.85 g) in ethanol in a hydrogenation reactor at 50° C. under hydrogen at 5 bar for 5 hours. The mixture was cooled, filtered and evaporated to give a 95/5 mixture of 2-chloro-4-trifluoromethylaniline and 2-chloro-5-trifluoromethylaniline (33.1 g). Hydrogen chloride gas was added over 0.5 hour to a solution of the above mixture in ethanol and chlorobenzene, cooled to 0° C., and filtered to give 2-chloro-4-trifluoromethylaniline hydrochloride (33.5 g), having a purity of >99%. The overall yield from 3,4-dichlorobenzotrifluoride was 85%.

What is claimed is:

1. A process for preparing a compound of formula (I):

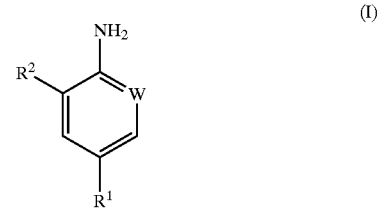

(I)

wherein R is haloalkyl, haloalkoxy or $-SF_5$; W is N or $CR^3$; and $R^2$ and $R^3$ are each independently hydrogen or chlorine; or an acid addition salt thereof; the process comprising the hydrogenolysis of a compound of formula (II):

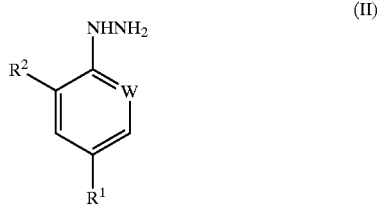

(II)

or an acid addition salt thereof, in the presence of a metal, a metal compound or a metal salt under reducing conditions.

2. A process according to claim 1, wherein the metal compound comprises Raney nickel.

3. A process according to claim 1, wherein the compound of formula (II) is prepared by reacting a compound of formula (III):

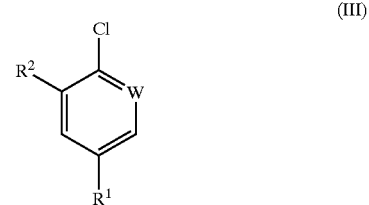

(III)

wherein $R^1$, $R^2$ and W are as hereinbefore defined, with hydrazine or an acid addition salt or source thereof.

4. A process according to claim 3, wherein hydrazine hydrate is used.

5. A process according to claim 1, wherein the compound of formula (I) is purified by precipitation of the salt formed by treatment with a strong acid in the presence of an organic solvent.

6. A process according to claim 5, wherein the salt is the hydrochloride salt and the solvent is an alcohol or a halogenated aromatic compound.

7. A process according to claim 1, wherein $R^1$ is trifluoromethyl, W is $CR^3$, $R^2$ is chlorine and $R^3$ is hydrogen.

8. A process according to claim 1, further comprising reacting the compound of formula (I) wherein one or both of $R^2$ and $R^3$ represent a hydrogen atom, with a chlorinating agent to replace the or each hydrogen atom represented by $R^2$ and $R^3$ and give the corresponding compound of formula (I) where $R^2$ and $R^3$ are each chlorine.

9. A process according to claim 1, wherein the compound of formula (I) is diazotized to give a compound of formula (IV):

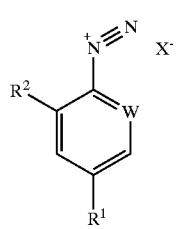

where $R^1$, $R^2$ and $R^3$ are as defined above and X is an anion; the compound of formula (IV) is further reacted with a compound of formula (V):

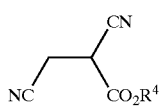

where $R^4$ is $C_{1-6}$ alkyl, and, optionally reacted with a base to prepare a compound of formula (VI):

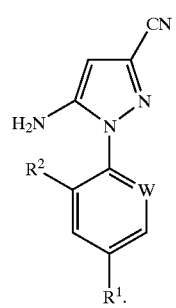

10. A process according to claim 1, wherein $R^1$ is trifluoromethyl, trifluoromethoxy or $-SF_5$.

11. A process according to claim 10, wherein $R^1$ is trifluoromethyl.

12. A process according to claim 9, wherein the compound of formula (VI) is converted to a compound of formula (VII):

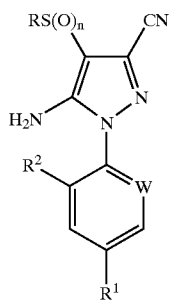

wherein R is alkyl or haloalkyl and n is 0, 1 or 2.

13. A process according to claim 12, wherein the compound of formula (VII) is 5-amino-1-(2,6-dichloro-4-trifluoromethylphenyl)-3-cyano-4-trifluoromethylsulphinylpyrazole (fipronil) or 5-amino-1-(2,6-dichloro-4-trifluoromethylphenyl)-3-cyano-4-ethylsulphinylpyrazole (ethiprole).

14. A process according to claim 1, wherein hydrogenolysis is conducted in the presence of hydrogen and Raney nickel, at a pressure of 2 to 20 bars and a temperature of 20° to 150° C.

15. A process which comprises:
(a) reducing a compound of formula (II):

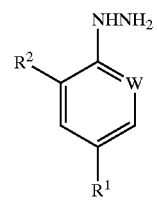

to yield a compound of formula (I):

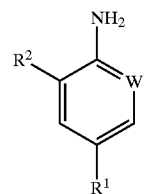

where $R^1$ is haloalkyl, haloalkoxy or $-SF_5$; W is N or $CR^3$; and $R^2$ and $R^3$ are each independently hydrogen or chlorine; or an acid addition salt thereof;
(b) reacting a compound of formula (I) with a diazotizing agent to give a compound of formula (IV):

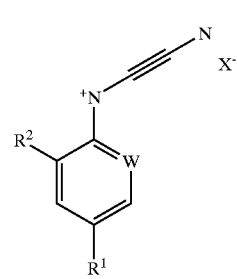

where X is an anion;

(c) reacting a compound of formula (IV) with a compound of formula (V):

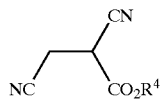
(V)

where $R^4$ is $C_{1-6}$ alkyl to form a reaction product;

(d) contacting said reaction product with a base to form a compound of formula (VI):

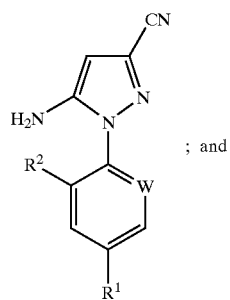
(VI)

; and (e) reacting a compound of formula (VI) with an oxidizing agent and R—S—Hal to form a compound of the formula (VII):

(VII)

where R is alkyl or haloalkyl and n is 0–2.

16. A process according to claim 15, wherein the compound of formula (II) is prepared by reacting a compound of formula (III);

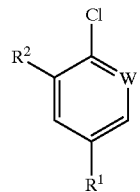
(III)

with hydrazine, an acid salt thereof or a source thereof.

* * * * *